(12) United States Patent
Lyons

(10) Patent No.: US 11,497,416 B1
(45) Date of Patent: Nov. 15, 2022

(54) POSTURAL AWARENESS DEVICE

(71) Applicant: Anne Katherine Lyons, Shoreline, WA (US)

(72) Inventor: Anne Katherine Lyons, Shoreline, WA (US)

( * ) Notice: Subject to any disclaimer, the term of this patent is extended or adjusted under 35 U.S.C. 154(b) by 516 days.

(21) Appl. No.: 16/504,052

(22) Filed: Jul. 5, 2019

(51) Int. Cl.
*A61B 5/11* (2006.01)
*A61B 5/00* (2006.01)
*A61B 17/70* (2006.01)
*A63B 23/02* (2006.01)

(52) U.S. Cl.
CPC .......... *A61B 5/1116* (2013.01); *A61B 5/4561* (2013.01); *A61B 17/70* (2013.01); *A61B 5/6822* (2013.01); *A61B 5/6823* (2013.01); *A63B 23/0244* (2013.01)

(58) Field of Classification Search
CPC ............................ A61B 5/1116; A61B 5/4561
See application file for complete search history.

(56) References Cited

U.S. PATENT DOCUMENTS

| | | | | |
|---|---|---|---|---|
| 5,199,940 A | * | 4/1993 | Morris | A61F 5/055 128/845 |
| 5,337,758 A | * | 8/1994 | Moore | A61B 5/1116 473/209 |
| 2015/0065919 A1 | * | 3/2015 | Cuevas | A61B 5/1121 600/587 |
| 2016/0140826 A1 | * | 5/2016 | Sahiholnasab | A61B 5/4561 340/573.7 |

* cited by examiner

*Primary Examiner* — Alex M Valvis
*Assistant Examiner* — Yasmeen S Warsi
(74) *Attorney, Agent, or Firm* — Plager Schack LLP; Mark H. Plager; Kara Verryt

(57) ABSTRACT

A postural awareness device designed to improve an individual's posture may include a vertical core designed to be positioned vertically along a user's back; a cervical cradle attached to an upper portion of the vertical core, the cervical cradle designed to be positioned in alignment with a user's cervical spine; a thoracic cradle attached to a central portion of the vertical core, the thoracic cradle designed to be positioned in alignment with a user's thoracic spine; and a lumbosacral cradle attached to a bottom portion of the vertical core, the lumbosacral cradle designed to be positioned in alignment with a user's lumbar spine.

8 Claims, 4 Drawing Sheets

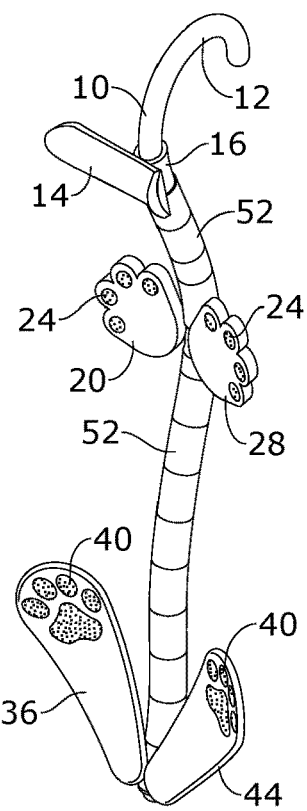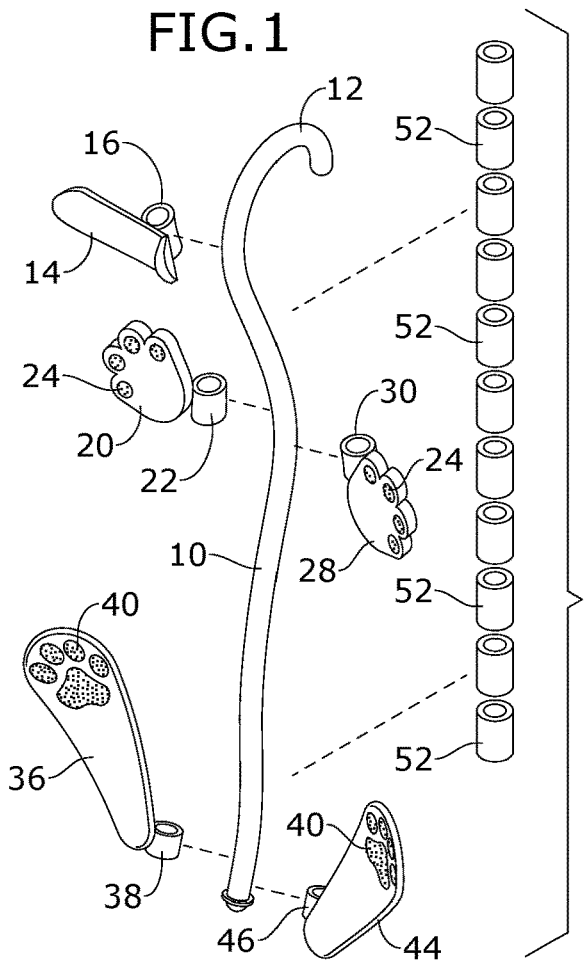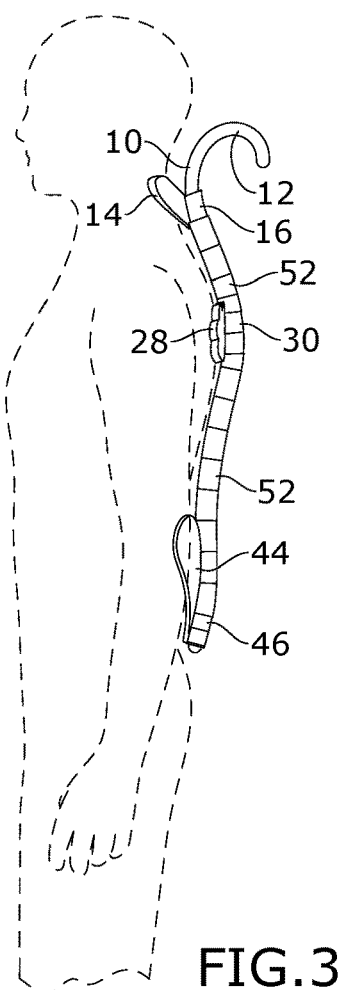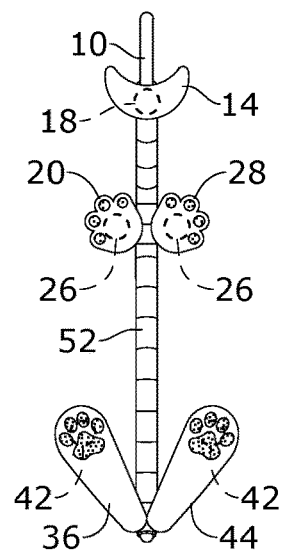
FIG.1
FIG.2
FIG.3
FIG.4

POSTURAL AWARENESS DEVICE

BACKGROUND

The embodiments herein relate generally to postural awareness devices, and more particularly, to a postural awareness device designed to improve sitting or standing posture in all populations, including the differently abled.

Many individuals have poor posture when sitting and/or standing, which can contribute to neck, upper back, and lower back discomfort. While posture devices exist, the existing devices are typically limited to support of one aspect of the spine and do not address the entire spine in a longitudinal plane.

Therefore, what is needed is a postural awareness device designed to encourage upright posture with specific tactile cues built into a longitudinal support structure to address cervical, thoracic, and lumbosacral spinal components simultaneously and gently.

SUMMARY

Some embodiments of the present disclosure include a postural awareness device designed to improve an individual's posture. The postural awareness device may include a vertical core designed to be positioned vertically along a user's back; a cervical cradle attached to an upper portion of the vertical core, the cervical cradle designed to be positioned in alignment with a user's cervical spine; a thoracic cradle attached to a central portion of the vertical core, the thoracic cradle designed to be positioned in alignment with a user's thoracic spine; and a lumbosacral cradle attached to a bottom portion of the vertical core, the lumbosacral cradle designed to be positioned in alignment with a user's lumbar spine.

BRIEF DESCRIPTION OF THE FIGURES

The detailed description of some embodiments of the invention is made below with reference to the accompanying figures, wherein like numerals represent corresponding parts of the figures.

FIG. 1 is a perspective view of one embodiment of the present disclosure.

FIG. 2 is an exploded view of one embodiment of the present disclosure.

FIG. 3 is a side view of one embodiment of the present disclosure, shown in use.

FIG. 4 is a front view of one embodiment of the present disclosure.

DETAILED DESCRIPTION OF CERTAIN EMBODIMENTS

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used as a postural awareness device and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

a. Extendable Core
    b. Cervical Cradle
    c. Thoracic Cradles
    d. Lumbosacral Cradles The various elements of the device of the present disclosure may be related in the following exemplary fashion. It is not intended to limit the scope or nature of the relationships between the various elements and the following examples are presented as illustrative examples only.

Figure 14:
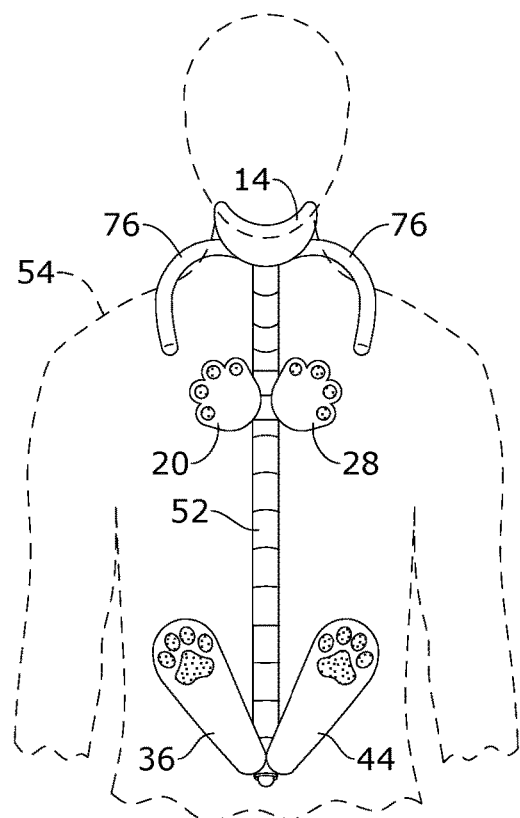
FIG. 14 is a front view of one embodiment of the present disclosure.
Figure 15:
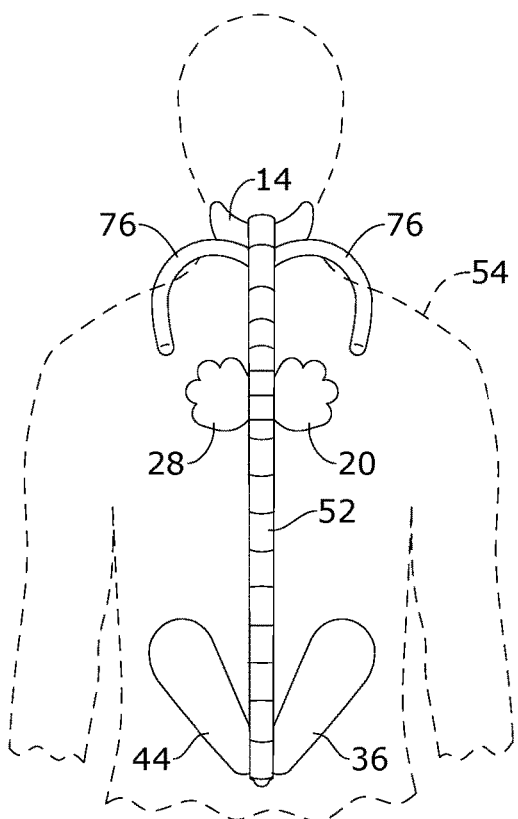
FIG. 15 is a rear view of one embodiment of the present disclosure.

By way of example, and referring to FIGS. 1-15, some embodiments of the present disclosure include a postural awareness device designed to improve an individual's sitting or standing posture, the device comprising a vertical core 10 designed to be positioned vertically along a user's back; a cervical cradle 14 attached to an upper portion of the vertical core 10; a thoracic cradle attached to a central portion of the vertical core 10; and a lumbosacral cradle attached to a bottom portion of the vertical core 10. As shown in the Figures, some embodiments of the device comprise a right thoracic cradle 20 and a left thoracic cradle 28 attached to the central portion of the vertical core 10 and a right lumbosacral cradle 36 and a left lumbosacral cradle 44 attached to a bottom portion of the vertical core 10. In embodiments, such as those shown in FIGS. 1-3, an upper most end of the core 10 may comprise at least one hook 12. The at least one hook 12 may resemble a curved cattail, wherein the hook 12 may be used to hook the device over a chair back or other object. Alternatively, as shown in FIGS. 14 and 15, the upper most end of the core 10 may comprise a pair of shoulder hooks 76 designed to hook over a user's shoulders. Thus, the end of the core 10 may either curve away from the user, as shown with the at least one hook 12, or toward the user, as shown with the pair of shoulder hooks 76.

Figure 5:
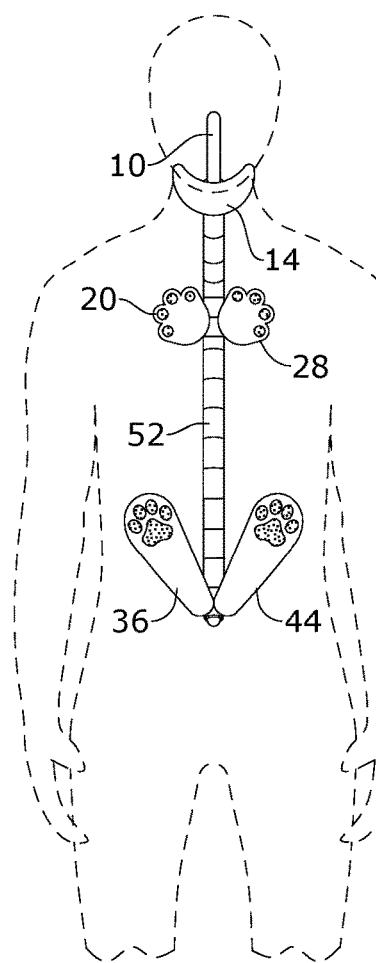
FIG. 5 is a front view of one embodiment of the present disclosure.
Figure 7:
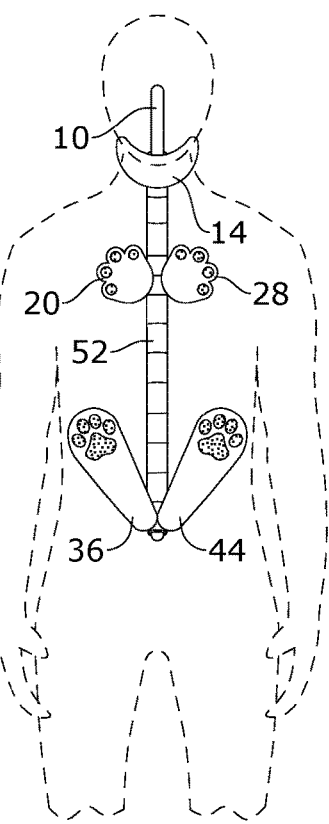
FIG. 7 is a front view of one embodiment of the present disclosure.

As shown in the Figures, the core 10 may comprise a plurality of extension gaskets 52 positioned along a length of the core 10. The extension gaskets 52 may provide for a way to lengthen or shorten the device, as desired. To lengthen the device, additional extension gaskets 52 may be placed onto the core 10 by threading the core 10 through the extension gaskets 52, thus accommodating a taller individual, as shown in FIG. 5. Alternatively, to shorten the device, extension gaskets 52 may be removed from the core 10, thus accommodating a shorter user, as shown in FIG. 7. As a result, the device of the present disclosure may have a customizable and adjustable length to accommodate users of varying heights.

As described above, the core 10 may have a cervical cradle 14, a right thoracic cradle 20, a left thoracic cradle 28, a right lumbosacral cradle 36, and a left lumbosacral cradle 44 attached thereto. For example, each of the cradles 14, 20, 28, 36, 44 may have an attachment ring extending from a surface thereof, wherein the attachment ring may be used to attach the cradle to the core 10. Specifically, the attachment rings may comprise a channel extending therethrough such that the core 10 may be threaded through the channel.

The cervical cradle 14 may be elongate, curved, and contoured so as to accommodate a user's cervical spine area. As shown in FIG. 4, the cervical cradle 14 may resemble a cat's head with ears. A cervical attachment ring 14 may extend from a back surface thereof, wherein the back surface may be the surface facing away from a user. The cervical cradle 14 may be positioned on a portion of the core 10 to align with the user's cervical spine when the device is in use.

Figure 6:
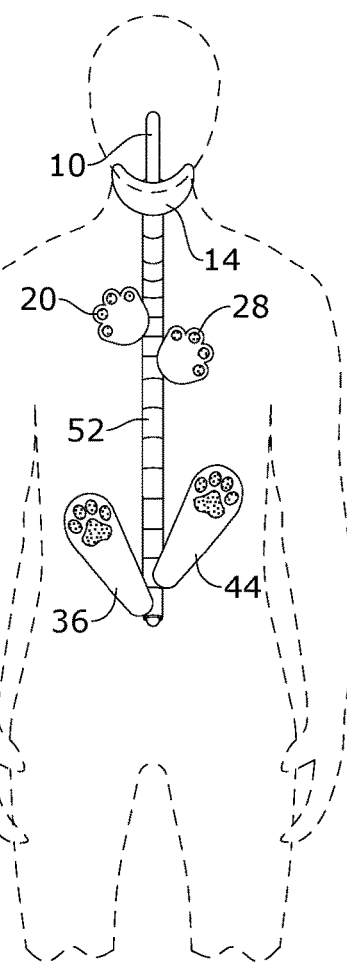
FIG. 6 is a front view of one embodiment of the present disclosure.

The thoracic cradles 20, 28 may have any shape and size suitable for aligning with a user's thoracic spine area. In some embodiments, and as shown in the Figures, the thoracic cradles 20, 28 may each resemble a cat's front paw. Each of the right thoracic cradle 20 and the left thoracic cradle 28 may comprise a front side and a back side, wherein the front side may be the surface of the cradle 20, 28 designed to be positioned against a user 54. When looking at the front side of the right thoracic cradle 20, a thoracic attachment ring 22 may extend from a rightmost portion of the right thoracic cradle 20. When looking at the front side of the left thoracic cradle 28, a thoracic attachment ring 30 may extend from a leftmost portion of the left thoracic cradle 28. Thus, the right thoracic cradle 20 may be a mirror image of the left thoracic cradle 28. In embodiments, the front side of the right and left thoracic cradles 20, 28 may include non-skid pads 24 attached thereto. The non-skid pads 24 may be substantially circular in shape, as shown in the Figures; however, other shapes and sizes are envisioned. In embodiments, the right thoracic cradle 20 and the left thoracic cradle 28 may be two separate components of the device, meaning they are not physically attached to one another. As such, a user may positioned the thoracic attachment rings 22, 30 such that the thoracic cradles 20, 28 are symmetrically positioned with respect to a user's spine. Alternatively, as shown in FIG. 6, one of the thoracic cradles 20, 28 may be positioned higher or lower along the core 10 to result in asymmetrical positioning of the thoracic cradles 20, 28 with respect to the user's spine.

The lumbosacral cradles 36, 44 may have any size and shape suitable for aligning with a user's lumbar spine area. In some embodiments, and as shown in the Figures, each of the lumbosacral cradles 36, 44 may resemble a cat's rear paw. Thus, the lumbosacral cradles 36, 44 may each be elongate, rounded, and contoured to accommodate a user's lumbar spine area. Each of the right lumbosacral cradle 36 and the left lumbosacral cradle 44 may comprise a front side and a back side, wherein the front side may be the surface of the cradle 36, 44 designed to be positioned against a user 54. When looking at the front side of the right lumbosacral cradle 36, a lumbosacral attachment ring 38 may extend from a rightmost portion of the right lumbosacral cradle 36. When looking at the front side of the left lumbosacral cradle 44, a thoracic attachment ring 46 may extend from a leftmost portion of the left lumbosacral cradle 44. Thus, the right lumbosacral cradle 36 may be a mirror image of the left lumbosacral cradle 44. In embodiments, the front side of the lumbosacral cradles 36, 44 may include non-skid pads 40 attached thereto. While the use of any size or shape non-skid pads are envisioned, in some embodiments, the non-skid pads 40 may be substantially paw print shaped. In embodiments, the right lumbosacral cradle 36 and the left lumbosacral cradle 44 may be two separate components of the device. Thus, similar to the thoracic cradles 20, 28, the lumbosacral attachment rings 38, 46 may be positioned such that the lumbosacral cradles 36, 44 are symmetrically positioned with respect to a user's spine. Alternatively, as shown in FIG. 6, one of the lumbosacral cradles 36, 44 may be positioned higher or lower along the core 10 to result in asymmetrical positioning of the lumbosacral cradles 36, 44 with respect to the user's spine.

As shown in FIG. 4, each of the cradles may optionally include a sensor built therein. For example, the cervical cradle 14 may include a cervical sensor 18 built therein, the thoracic cradles 20, 28, may each include a thoracic sensor 26 built therein, and the lumbosacral cradles 36, 44 may each include a lumbosacral sensor 42 built therein. The sensors may each be embedded into the surface of the cradles, wherein the sensor may be activated when pressure is placed onto the surface of each of the cradles. In embodiments, when the sensors are activated, the device may alert the user that a more erect posture has been achieved. For example, when each of the sensors is activated, the device may produce an audible sound, such as a purring sound for a predetermined period of time, such as several seconds, to alert the user. The sensors may be any suitable type of sensor; however, in some embodiments, the sensors may comprise haptic sensors. Specifically, the haptic sensors may be embedded into the cervical cradle 14, thoracic cradles 20, 28, and the lumbosacral cradles 36, 44, wherein pressure or muscle activation generated by erect posture against the sensors transmits information to a control system/activator (not shown) that may respond with complex vibration patterns to purr and reinforce and promote user concentration and focus, despite competing environmental stimuli, to maintain erect posture with chin tuck, scapular squeeze with shoulder depression, and core abdominal contraction while seated, standing, or walking. This may guide, enhance, and reinforce erect posture through periodic tactile cues to instruct a corrective movement change, which may ultimately lead to improved self-correction of posture.

Figure 8:
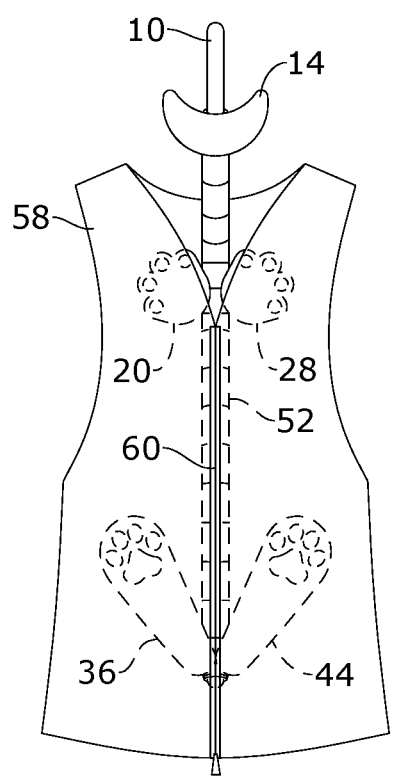
FIG. 8 is a front view of one embodiment of the present disclosure.
Figure 9:
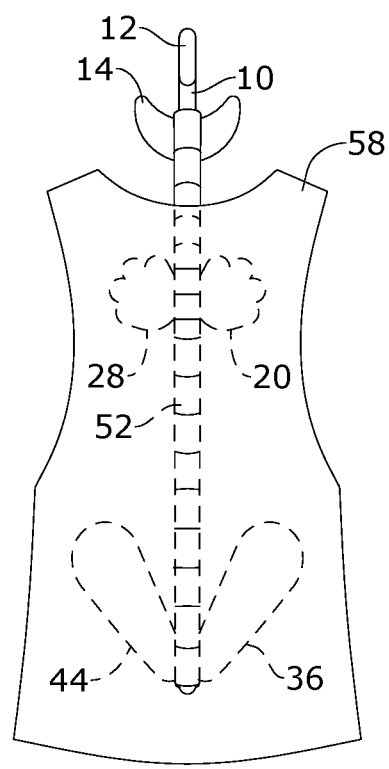
FIG. 9 is a rear view of one embodiment of the present disclosure.
Figure 10:
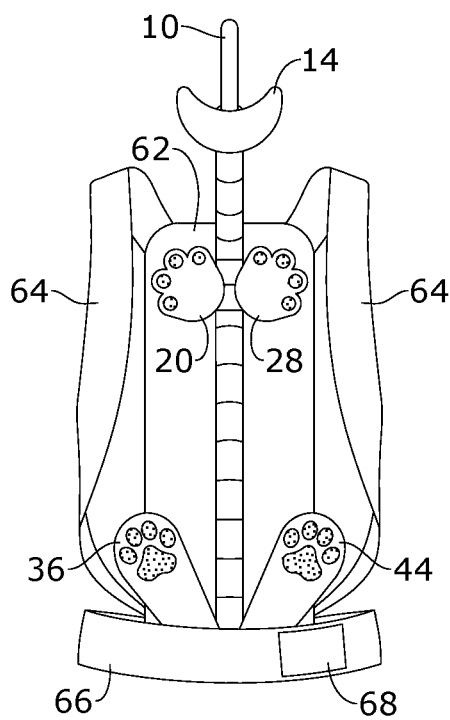
FIG. 10 is a front view of one embodiment of the present disclosure.
Figure 11:
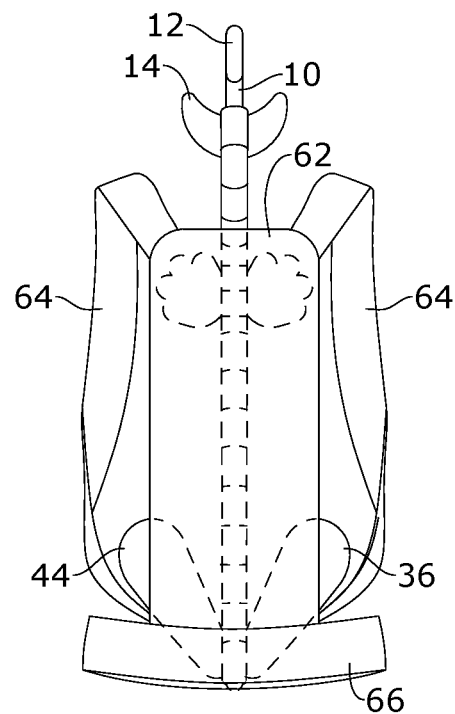
FIG. 11 is a rear view of one embodiment of the present disclosure.
Figure 12:
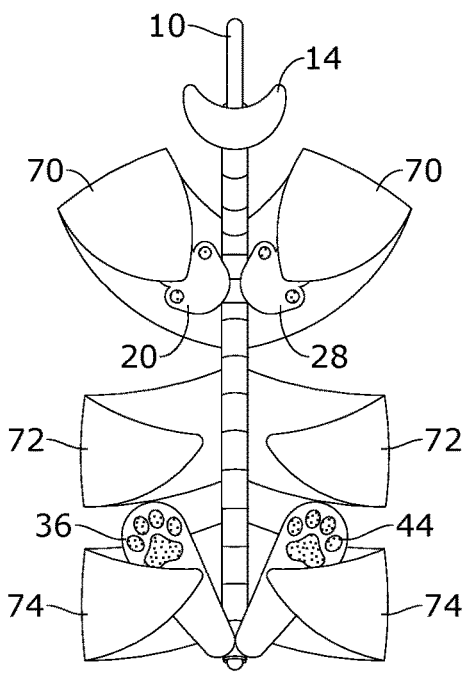
FIG. 12 is a front view of one embodiment of the present disclosure.
Figure 13:
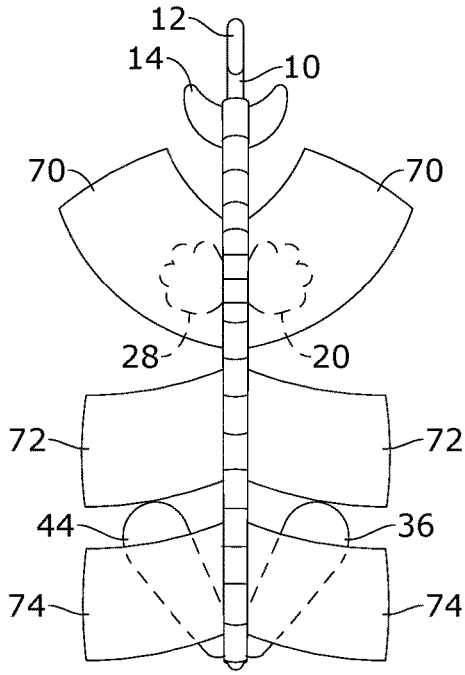
FIG. 13 is a rear view of one embodiment of the present disclosure.

Some embodiments of the postural device of the present disclosure, such as those shown in FIGS. 8-13, may further include components allowing the device to be wearable or otherwise secured to a user. As shown in FIGS. 8 and 9, the device may further comprise a vest 58 operatively attached to the core 10. The vest 58 may include a fastener, such as a zipper 60, to secure the vest around the user's torso. Alternatively, as shown in FIGS. 10 and 11, the device may be a backpack like device, wherein the device further comprises a backboard 62 operatively attached to the core 10. The backboard 62 may include a pair of shoulder straps 64 extending therefrom, the straps 64 each designed to be worn like backpack straps and a waist strap 66 designed to encircle a user's waist. The waist strap 66 may include optional features, such as a pocket 68. Yet further embodiments of the postural awareness device may comprise shell pieces designed to secure the device to the user. For example, the device may further comprise an upper hinged shell piece 70 designed to extend along a user's upper back and over his or her shoulders, a middle hinged shell piece 72 designed to extend along a user's middle back and around his or her waist, and a lower hinged shell piece 74 designed to extend along a user's lower back and around his or her hips.

The device of the present disclosure may be made of any suitable or desired materials. In some embodiments, the different components may comprise a flexible foam material to provide gentle and comfortable postural support and awareness, although the use of other materials are envisioned.

To use the device of the present disclosure, the user may determine the correct length of the core 10 by adding or subtracting extension gaskets 52. The cradles may be positioned along the core 10 at their desired positions to place gentle pressure on the user's different back portions while in use. If the user will be sitting, he or she may simply place the hooked end 12 over a chair back and then sit as normal. Alternatively, if the user will be mobile, the user may wear a version of the device with wearable components, such as the vest or backpack. To improve posture, the user may ensure positioning his or her back to place pressure on each of the cradles. In embodiments with the embedded sensors, placing pressure on each of the cradles may produce an alert.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A postural awareness device designed to improve an individual's posture, the device comprising:
    a vertical core designed to be positioned vertically along a user's back;
    a cervical cradle attached to an upper portion of the vertical core, the cervical cradle designed to be positioned in alignment with a user's cervical spine;
    a right thoracic cradle and a left thoracic cradle each individually attached to a central portion of the vertical core, the right thoracic cradle and the left thoracic cradle each designed to be positioned in alignment with a user's thoracic spine;
    a right lumbosacral cradle and a left lumbosacral cradle each individually attached to a bottom portion of the vertical core, the right lumbosacral cradle and the left lumbosacral cradle each designed to be positioned in alignment with a user's lumbar spine;
    a cervical attachment ring extending from the cervical cradle, the cervical attachment ring designed to removably engage with the vertical core;
    a thoracic attachment ring extending from the thoracic cradle, the thoracic attachment ring designed to removably engage with the vertical core; and
    a lumbosacral attachment ring extending from the lumbosacral cradle, the lumbosacral ring designed to removably engage with the vertical core,
    wherein:
        the cervical cradle, the right thoracic cradle, the left thoracic cradle, the right lumbosacral cradle, and the left lumbosacral cradle each comprise a respective shaped plate;
        each of the right thoracic cradle and the left thoracic cradle are independently adjustable along a length of the vertical core; and
        each of the right lumbosacral cradle and the left lumbosacral cradle are independently adjustable along the length of the vertical core.

2. The postural awareness device of claim 1, further comprising at least one non-skid pad on a front surface of the thoracic cradle.

3. The postural awareness device of claim 1, further comprising at least one non-skid pad on a front surface of the lumbosacral cradle.

4. The postural awareness device of claim 1, further comprising a plurality of extension gaskets threaded along a length of the vertical core.

5. The postural awareness device of claim 1, further comprising a sensor embedded into each of the cervical cradle, the thoracic cradle, and the lumbosacral cradle, the sensor designed to sense whether pressure is placed on each of the cervical cradle, the thoracic cradle, and the lumbosacral cradle.

6. The postural awareness device of claim 1, further comprising a vest operatively attached to the vertical core.

7. The postural awareness device of claim 1, further comprising a backboard with a pair of shoulder straps and a waist strap extending therefrom, the backboard operatively attached to the vertical core.

8. The postural awareness device of claim 1, further comprising a plurality of shell pieces operatively attached to the vertical core, the plurality of shell pieces designed to at least partially encircle a user.

* * * * *